(12) United States Patent
Asjes et al.

(10) Patent No.: US 8,731,633 B2
(45) Date of Patent: May 20, 2014

(54) DEVICE FOR POSITIONING ELECTRODES ON A USER'S SCALP

(75) Inventors: Ronald Jan Asjes, Valkenswaard (NL); Mark Christoph Jaeger, Veldhoven (NL); Sima Asvadi, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 77 days.

(21) Appl. No.: 13/504,220

(22) PCT Filed: Nov. 2, 2010

(86) PCT No.: PCT/IB2010/054943
§ 371 (c)(1),
(2), (4) Date: Apr. 26, 2012

(87) PCT Pub. No.: WO2011/055291
PCT Pub. Date: May 12, 2011

(65) Prior Publication Data
US 2012/0226127 A1  Sep. 6, 2012

(30) Foreign Application Priority Data
Nov. 4, 2009  (EP) .................................... 09175008

(51) Int. Cl.
*A61B 5/0478* (2006.01)
*A61B 5/0476* (2006.01)

(52) U.S. Cl.
USPC .......................................... 600/383; 600/544

(58) Field of Classification Search
CPC ... A61B 5/0476; A61B 5/0478; A61B 5/6803
USPC ................................................... 600/383, 544
See application file for complete search history.

(56) References Cited

U.S. PATENT DOCUMENTS

| | | |
|---|---|---|
| 3,411,495 A | 11/1968 | Casby |
| 4,967,038 A | 10/1990 | Gevins et al. |
| 5,038,782 A | 8/1991 | Gevins et al. |
| 5,740,812 A | 4/1998 | Cowan |
| 6,067,464 A * | 5/2000 | Musha .......................... 600/383 |

(Continued)

FOREIGN PATENT DOCUMENTS

| | | |
|---|---|---|
| GB | 2396421 A | 6/2004 |
| RU | 2071721 C1 | 1/1997 |

(Continued)

OTHER PUBLICATIONS

Deiss et al: "A Brain-Machine Interface Using Dry-Contact, Low-Noise EEG Sensors"; IEEE International Symposium on Circuits and Systems, 2008, pp. 1986-1989.

*Primary Examiner* — Lee S Cohen

(57) ABSTRACT

A device (1) is described for positioning electrodes on a user's scalp. It comprises a housing (3), for example a headpiece of a headphones device, which can be put around a user's head. An elastic element (11) and a plurality of electrodes are positioned, so that once the housing (3) is put around the user's head, the elastic element (11) at least partly follows the curvature of the user's head. The stress in the elastic element (11) due to stretching thereof caused by putting the housing around the user's head causes the elastic element (11) to exert pressure on at least some of the plurality of electrodes towards the scalp. Hereby, effective contact of the plurality of electrodes to the scalp is facilitated.

18 Claims, 4 Drawing Sheets

(56) References Cited

U.S. PATENT DOCUMENTS

| | | |
|---|---|---|
| 6,708,051 B1 * | 3/2004 | Durousseau .................. 600/383 |
| 2006/0217632 A1 | 9/2006 | Causevic et al. |
| 2007/0093706 A1 | 4/2007 | Gevins et al. |
| 2008/0027345 A1 * | 1/2008 | Kumada et al. ............... 600/544 |
| 2009/0150919 A1 | 6/2009 | Lee et al. |
| 2010/0198042 A1 * | 8/2010 | Popescu et al. ............... 600/383 |

FOREIGN PATENT DOCUMENTS

| | | |
|---|---|---|
| WO | 0045701 A1 | 8/2000 |
| WO | 2008067839 A1 | 6/2008 |
| WO | 2008109699 A2 | 9/2008 |

* cited by examiner

DEVICE FOR POSITIONING ELECTRODES ON A USER'S SCALP

BACKGROUND OF THE INVENTION

The present invention relates to the field of measuring electric brain activity and more specifically to the positioning of electrodes on a user's scalp for this purpose.

In order to measure electric brain activity a device is required with electrodes that are in contact with the user's head. Such devices are well known for providing medical diagnostics, for example for electroencephalography (EEG). The main challenge in applying EEG electrodes is to get a low impedance contact to the scalp. In clinical measurements this is normally done with an elastic cap with integrated Ag/AgCl coated metal cups. The skin underneath these cups is usually prepared by degreasing and often additional abrasion, i.e. removal of the dry top layer of the scalp. The cups are filled afterwards with gel. This assures a low ohmic contact to the deeper skin layer and a 'conversion' from ionic current in the body to electron current in the measuring system. Using conductive gel also partly solves the problem of the varying distance between the metal contact and the skin due to the variation from person to person of the hair layer thickness.

For non-medical applications like sports and life style consumer products it is not practical to use these kind of 'wet' electrodes and perform the skin preparation essential for their function. There are a number of solutions and investigations aiming at realizing 'dry' electrodes.

WO 00/45701 discloses such a 'dry' electrode solution. It discloses a headgear, which includes a front forehead pad, a base strap assembly connected to the front forehead pad, a plurality of EEG electrode locators for receiving EEG electrodes, and a plurality of locator straps connected to the front pad of material, the base trap assembly, and to the plurality of EEG electrode locators for accurately positioning the plurality of EEG electrode locators positioned relative to the scalp of a user. A visor can be attached to the front pad of material, and the base strap assembly may include an occipital locator device. A plunger assembly with spreadable fingers for optionally parting the hair of the user's scalp is also provided that is inserted in the electrode locators to optionally prepare the user's scalp and to seat the electrodes. However, the headgear according to this publication requires that a user pushes each plunger assembly into contact with the scalp. So, the user needs to re-set the plunger assemblies to the initial positions every time the headgear is taken on and off.

SUMMARY OF THE INVENTION

It would be advantageous to provide a device for positioning electrodes on a user's scalp, which is easier to use.

To better address this concern, according to an aspect of the invention a device is provided for positioning a plurality of electrodes on a user's scalp for measuring electric brain activity, which comprises:

a unit configured to be put at least partly around a user's head; and at least an elastic element at the inner side of the unit.

The unit can also be described by the term "housing", without implying any limitations as to the construction of the device.

The device further comprises a positioning arrangement configured to position the elastic element and the electrodes, so that once the housing is put around the user's head, the elastic element at least partly follows the curvature of the user's head. Stress in the elastic element due to stretching thereof, which at its turn is caused by putting the housing around the user's head, causes the elastic element to exert pressure on at least some of the plurality of electrodes towards the scalp, thereby facilitating effective contact of the plurality of electrodes to the scalp. So, there is no need for manual adjustment by the user of the device or any external mechanism in order to exert the needed pressure for the electrodes to be in effective contact to the scalp.

The plurality of electrodes may be part of the device or they may be provided as external elements that have to be mounted by the user to the device.

According to an embodiment of the invention, the plurality of electrodes is mounted on flexible surfaces. This allows the individual electrodes to move in a flexible way in different directions. In case that the plurality of electrodes is divided in multiple arrays, the electrodes are enabled to follow the curvature of the scalp in order to make the required contact with the scalp involving as many electrodes as possible.

The housing may have the shape of a headband and be of firm material. It is for example a part of a headphones device. The elastic element may be an elastic band.

According to a further embodiment of the invention, the positioning arrangement further comprises a positioning strap at the inner side of the elastic band, which is fixed to a plurality of the flexible surfaces. The positioning strap comprising openings through which the electrodes protrude when the elastic band(s) exert pressure on the electrodes, once the housing is put around the user's head. As a result, the positions of the electrodes on the scalp are defined reliably and can be located as close as possible to the positions defined by the International 10/20 System that is well known in the art as the standard for positioning of EEG Electrodes. The weight of the housing defines largely the 'stress' in the positioning strap but has no influence on the pressure of the electrodes on the scalp. This force is set to a comfortable level by the separate elastic band running over the flexible surfaces, whereon the electrodes are mounted.

In case that the housing is a headpiece of a headphones device, the positioning arrangement may comprise two projection elements for projecting the ends of the positioning strap against the auricles of the user, when the housing is put around the user's head. In this way, the ears may be used as mechanical reference via the headphones.

To cope with the variety of head sizes and shapes, the positioning strap may be divided in multiple parts, which are mutually connected by one or more elastic connectors.

According to an alternative embodiment, the positioning arrangement further comprises for each of the flexible surfaces an individual projection unit connected to the inner side of the housing. The result is a simple structure to position the plurality of electrodes at the correct location on the scalp.

The flexible surfaces wherein the electrodes are embedded may be low viscosity rubber pads, which is a very suitable option for this purpose. For the electrical connection of the electrodes of the arrays metal foil may be used. An alternative solution for the electrical connection is the use of electrically conductive rubber.

According to a still further embodiment, the electrodes are metal pins with rounded ends to be in contact with the scalp. The rounded ends facilitates an easy passing of the pins through hair bundles to the skin (scalp) and help to give hair in between the pin and the skin the freedom to 'roll' away. With this shape there is also no irritation which may occur with sharp edges, used in prior art dry electrode devices. Due to the (low) pressure of the pins onto the relatively soft skin the contact area around the end increases. This lowers the contact resistance even further.

According to yet a further embodiment, the length of the electrodes is larger than 4 mm and smaller than 7 mm. In this way, the structure is largely insensitive to thicker hair layers. This is a 'comb or brush' principle.

The metal pin electrodes may be gold plated to assure an inert interface to the skin without possible corrosion problems due to the salt from the sweat, which furthermore is well cleanable. Gold is (like e.g. platinum) also non allergic. Other contact materials that are suitable as contact materials are carbon and several conductive polymers. Other metals like nickel, chromium and copper are less suitable because of health risks. Presently used contact materials for electrodes for measuring brain activity, such as silver with silver chloride coating and tin, although in principle usable for this purpose, may have corrosion problems after some time. Materials like stainless steel and aluminum have a natural oxide layer that reduces the conductivity to the skin. Ion containing polymers or ceramics, although in principle usable for this purpose, may lose their conductivity over time and due to cleaning.

These and other aspects of the invention will be apparent from and elucidated with reference to the embodiments described hereinafter.

BRIEF DESCRIPTION OF THE DRAWINGS

The invention will be better understood and its numerous objects and advantages will become more apparent to those skilled in the art by reference to the following drawings, in conjunction with the accompanying specification, in which.

Throughout the figures like reference numerals refer to like elements.

DETAILED DESCRIPTION OF THE PRESENT INVENTION

Figure 1:
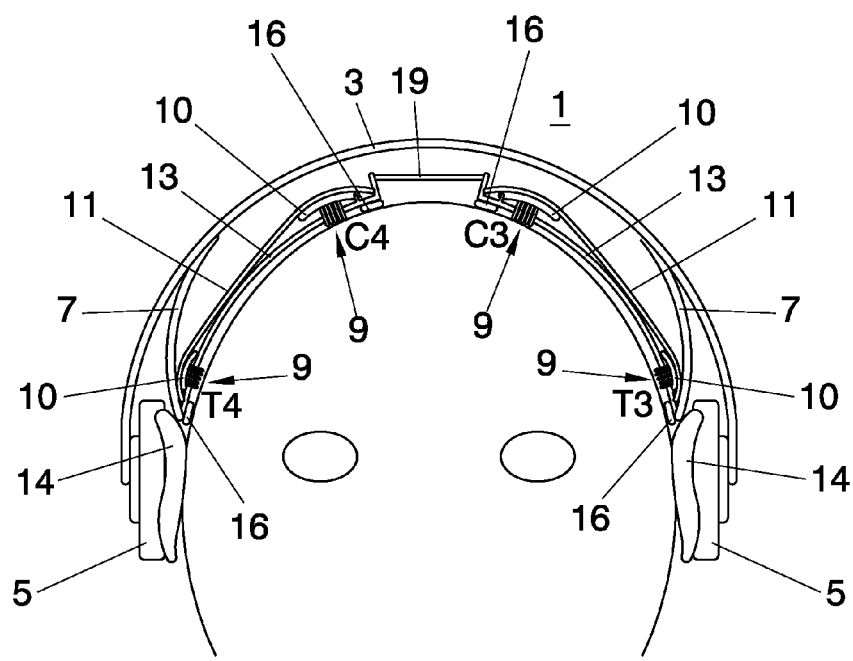
FIG. 1 shows a device according to a first exemplary embodiment of the present invention.
Figure 2:
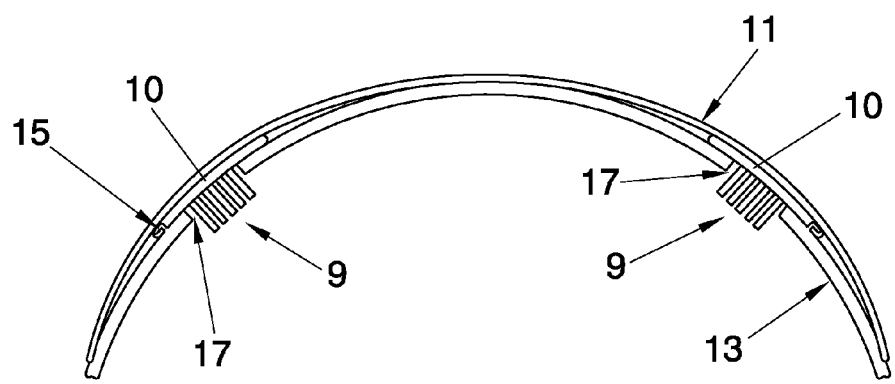
FIG. 2 shows a front view of some of the arrays of electrodes, the positioning strap and the elastic band of the device of FIG. 1.
Figure 3:
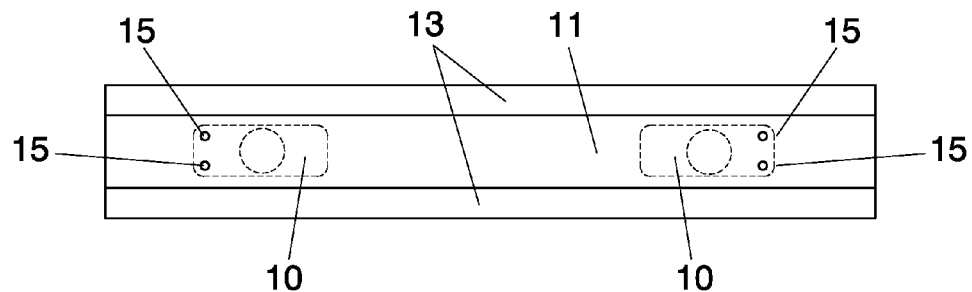
FIG. 3 shows a top view of the positioning strap and elastic band of the device of FIG. 1.
Figure 4:
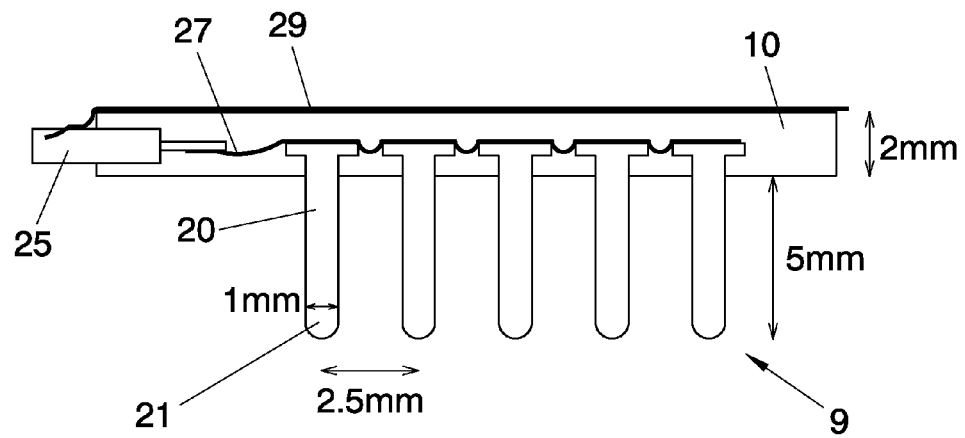
FIG. 4 shows a front view of an array of electrodes embedded in a rubber pad used in the device of FIG. 1.

FIG. 1 shows a device 1 for positioning electrodes on a user's scalp for measuring electric brain activity according to a first exemplary embodiment of the present invention. The device is a headphones comprising a headpiece 3 (also referred to in this description by "unit" or "housing"), made of firm but flexible material and having the shape of a headband, and earpieces 5. The device furthermore comprises a positioning arrangement consisting of two projection elements 7 and a positioning strap 13. The projection elements 7 are used for positioning a plurality of arrays 9 of electrodes (also referred to in this description by 'dry electrode structure') embedded in flexible surfaces 10, elastic elements (bands) 11 and the positioning strap 13 at the inner side of the housing 3. The two projection elements 7 project the ends of the positioning strap 13 against the auricles 14 of the user, when the housing is put around the user's head. At the inner side of the positioning strap small springs 16 are placed. The ends of the elastic bands 11 are also fixed to the projection elements 7 close to the points at which the ends of the positioning strap 13 are fixed to the projection elements 7. The positioning strap 13 is used for positioning the arrays of electrodes at predefined positions on the scalp. It is fixed to the plurality of the flexible surfaces 10 by means of fixations 15, as shown in FIGS. 2 and 3. It comprises openings 17 with a diameter of approximately 15 mm through which the electrodes of the arrays 9 protrude when the elastic bands 11 exert pressure on the electrodes. To cope with the variety in head sizes and shapes the positioning strap 13 is divided in two halves with a connecting elastic band 19 between them to guarantee good mechanical contact to the scalp all over the circumference. The reference electrode position of two of the arrays of electrodes is set by the spring loaded fixation point of the two halves of the positioning strap as close as possible to the T3/T4 locations of the International 10/20 System. The two halves of the positioning strap have the ears as mechanical reference via the main headphone-clamp The sense electrode arrays positioned at C3 and C4 according to the International 10/20 System (according to which C3-C4 refer to central sites for picking up the activity in the posterior regions of head) are fixed at the other ends of both of the positioning strap parts. In this way all electrode arrays are positioned in their right places in one simple action by just putting on the headphones in the usual way by the user.

Due to the stress on the elastic bands caused by the stretching thereof, which at its turn is caused by the insertion of the user's head in the housing (which pushes the positioning strap 13 and the elastic bands 11 upwards), the elastic bands 11 press the arrays of electrodes on the user's scalp, resulting in an effective contact of the electrodes to the scalp.

An eventually additional (active) body ground electrode, normally a wrist (-strap) electrode, could be added in the middle on top of the head (EEG Cz location). The body ground electrode is typically used in amplifiers for biosignal measuring to improve the signal quality.

Cabling and electronics, which may be integrated in the headphones or in an external device, are not depicted in FIGS. 1-3.

Figure 5:
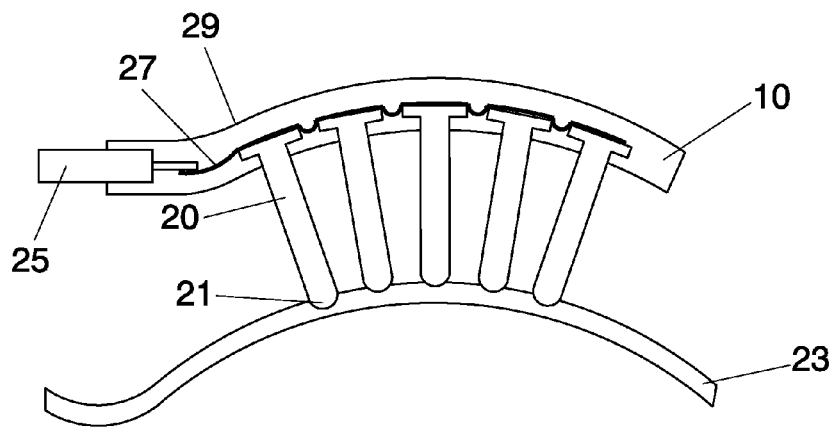
FIG. 5 shows the array of electrodes of FIG. 4 in contact with the scalp of a user.
Figure 6:
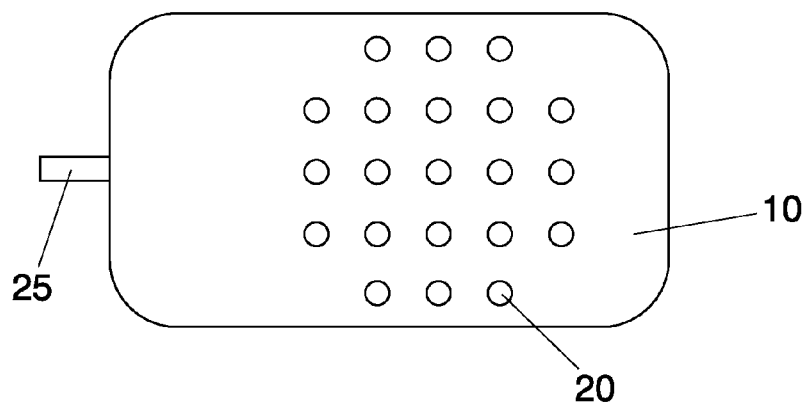
FIG. 6 shows an upper view of the rubber pad and the electrodes of FIG. 4.
Figure 7:
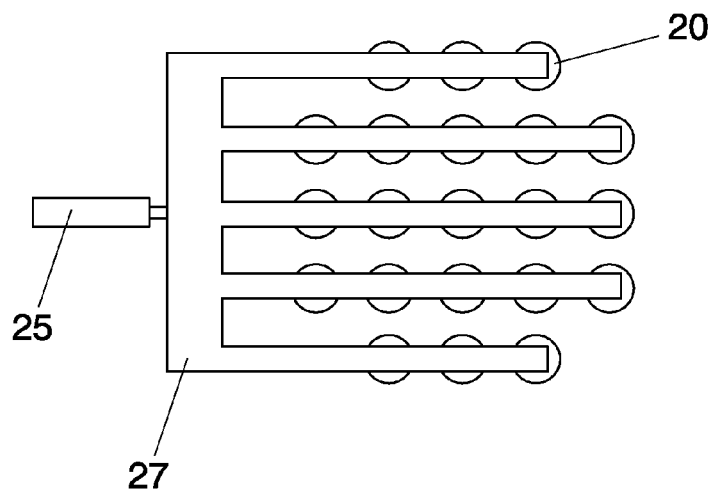
FIG. 7 shows the electrical connection of the array of electrodes of FIG. 4.

Now referring to FIGS. 4-7, an exemplary embodiment of implementing the arrays 9 of electrodes is described. The electrodes 20 are gold plated metal pins with a diameter of approximately 1 mm and placed at a distance to each other of 2.5 mm between their central axes. The pins have rounded (half spheres) ends 21. They are embedded in the flexible surface, a rubber pad, which is made of 2 mm thick, low viscosity, silicone rubber. This enables the structure to follow the curvature of the scalp 23 in order to make required contact with the skin involving as many pins as possible, as shown in FIG. 5. The pin length of the part of the pins not embedded in the rubber pad is approximately 5 mm. The pins are electrically connected to each other and to the cable 25 connecting to the electronic circuitry by means of a thin metal foil 27, for example of copper. The total array construction is covered with a thin metal foil 29 which is connected to the active shield of the cable 10. Alternatively, conductive rubber may be used as a base for the electrodes.

Testing of the device shown in FIGS. 1-7 test results showed that the dry electrodes can measure:
Difference in Eyes Open vs. Eyes Closed alpha activity and Difference in Relaxed vs. Mental Activity (Alpha Desynchronization).

Figure 8:
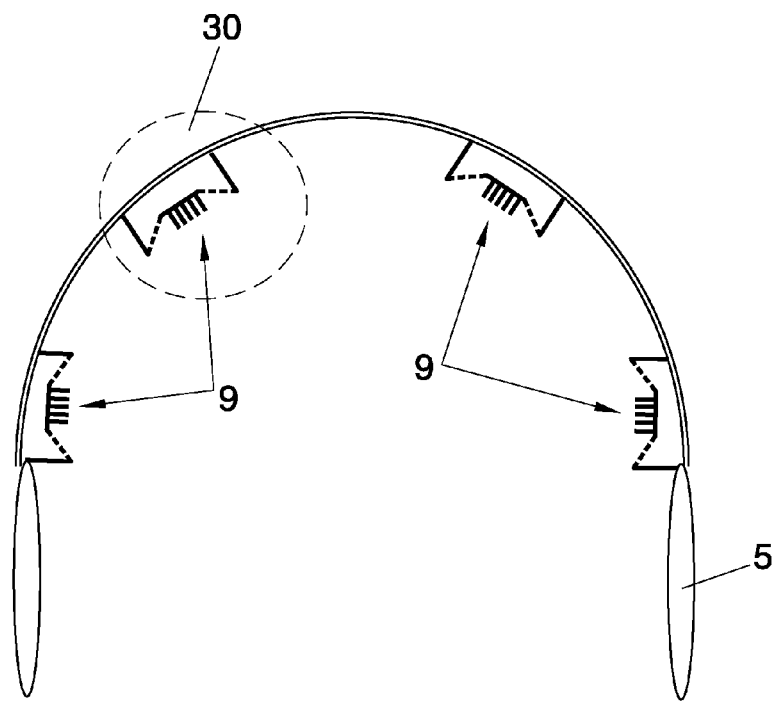
FIG. 8 shows a device according to a second exemplary embodiment of the present invention.
Figure 9:
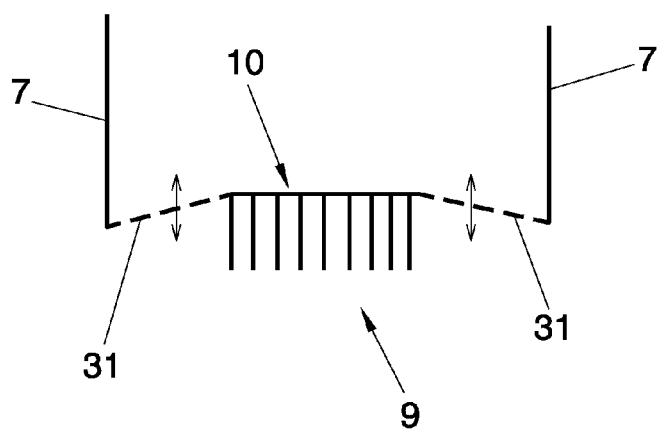
FIG. 9 shows an enlarged view of the mounting principle of the arrays of electrodes in the device of FIG. 8.

Now referring to FIGS. 8-9, a second exemplary embodiment is described of a device 1 for positioning electrodes on a user's scalp for measuring electric brain activity. The second exemplary embodiment assumes independent mounting of the arrays of electrodes 9 on the headpiece. The positioning of four arrays of electrodes 9 is depicted in FIG. 8. The mounting arrangement 30 of one of them is depicted detailed and enlarged in FIG. 9. A firm (plastic) housing 3 having the shape of a headband similar to a typical design of a headpiece for a normal headphones device is used as a support. On the inner side of the housing 3, for each array 9 of electrodes a projection unit is mounted, consisting of two projection elements 7 that support the electrodes.

Alternative ways of mounting the arrays of electrodes are possible, for example using two additional projection elements transverse to the ones depicted in FIG. 8 or using a cylindrical projection element that is supported by the headpiece 3.

The flexible dry electrode structure is attached to the projection elements by means of elastic bands that can be made of e.g., rubber or textile. The flexible surface used for electrode mounting can be an elastic pad on which the flexible dry electrode structure is positioned, similar to the embodiment depicted in FIGS. 1-3. This elastic pad is affixed to the elastic band connected to the two projection elements 7. In another embodiment the mounting is implemented by means of two elastic bands 31, each connecting one side of the flexible dry electrode structure to the projection elements 7 as depicted in FIG. 9. So, in this case the flexible surface 10 (elastic pad) is mounted between the two elastic bands 31. In case that another pair of projection elements is used, the mounting of the second (pair of) elastic band(s) can be done the same way as for the first pair.

The embodiment that includes cylindrical projection element has radial elastic bands that support the dry electrode structure. Furthermore, an elastic element of an elliptic shape mounted at the bottom part of the cylindrical projection element can be used instead of elastic bands to hold the dry electrode structure.

While the invention has been illustrated and described in detail in the drawings and foregoing description, such illustration and description are to be considered illustrative or exemplary and not restrictive; the invention is not limited to the disclosed embodiments.

In this regard it is to be noted that instead of arrays of electrodes, individual electrodes mounted on the elastic band may be used. Furthermore, the device may be something else than a headphones for example a (Alice) band, cap, helmet, glasses, etc. The electrodes can also be used for measuring ECG, EMG and EOG.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. Device positioned on a user's scalp for measuring electric brain activity, the device comprising:
a unit having the shape of a headband and configured to be put at least partly around a user's scalp;
a plurality of flexible surfaces;
a plurality of electrodes, the plurality of electrodes mounted on the plurality of flexible surfaces;
at least one elastic band, the at least one elastic band being fixed to a plurality of the flexible surfaces and being adapted to be disposed between the unit and the user's scalp; and
a positioning arrangement, the positioning arrangement comprising a positioning strap, the positioning strap being adapted to be disposed between the elastic band and the user's scalp, the positioning strap includes a plurality of openings through which the plurality of electrodes protrude when the unit is put around the user's scalp, wherein the positioning arrangement is configured to position the at least one elastic band and the electrodes, so that once the unit is put around the user's scalp, the at least one elastic band at least partly follows the curvature of the user's scalp and so that stress in the elastic band due to stretching thereof caused by putting the unit around the user's scalp causes the elastic band to exert pressure on at least some of the plurality of electrodes towards the scalp, thereby facilitating effective contact of the plurality of electrodes to the scalp.

2. Device according to claim 1, wherein the plurality of electrodes is divided in several arrays of electrodes.

3. Device according to claim 2, wherein the electrodes of at least one of the arrays are electrically connected to each other by means of metal foil.

4. Device according to claim 1, wherein the electrodes are metal pins with rounded ends to be in contact with the scalp.

5. Device according to claim 4, wherein the electrodes are gold plated.

6. Device according to claim 1, wherein the length of the electrodes is larger than 4 mm and smaller than 7 mm.

7. Device according to claim 1, further comprising one or more elastic connectors and wherein the positioning strap is divided in multiple parts, which are mutually connected by the one or more elastic connectors.

8. Device according to claim 1, wherein at least one of the flexible surfaces is a rubber pad.

9. Device according to claim 8, wherein the rubber is electrically conductive.

10. Device positioned on a user's scalp for measuring electric brain activity, the device comprising:
a unit configured to be put at least partly around a user's scalp;
a plurality of flexible surfaces;
a plurality of electrodes, the plurality of electrodes mounted on the plurality of flexible surfaces;
at least one elastic element, the at least one elastic element being adapted to be disposed between the unit and the user's scalp; and
a positioning arrangement comprising, for each of the flexible surfaces, an individual projection device connected to the unit and being adapted to be disposed between the unit and the user's scalp, wherein the positioning arrangement is configured to position the at least one elastic element and the electrodes, so that once the unit is put around the user's scalp, the at least one elastic element at least partly follows the curvature of the user's scalp and so that stress in the elastic element due to stretching thereof caused by putting the unit around the user's scalp causes the elastic element to exert pressure on at least some of the plurality of electrodes towards the scalp, thereby facilitating effective contact of the plurality of electrodes to the scalp.

11. Device according to claim 10, wherein the unit has the shape of a headband and wherein the at least one elastic element is an elastic band.

12. Device according to claim 10, wherein the at least one elastic element is fixed to the plurality of flexible surfaces and wherein the positioning arrangement further comprises a positioning strap, the positioning strap coupled to the projection device and being adapted to be disposed between the elastic element and the user's scalp, and the positioning strap comprising openings through which the electrodes protrude when the unit is put around the user's scalp.

13. Device according to claim 12, wherein the unit is a headpiece of a headphones device, and wherein the positioning strap has two ends so that, once the unit is put around the user's scalp, one end is associated with one of the user's auricles and the other end is associated with the other of the user's auricles, and wherein the positioning arrangement comprises two projection devices, the projection devices projecting the respective ends of the positioning strap against the respective auricles of the user once the unit is put around the user's scalp.

14. Device according to claim 12, further comprising one or more elastic connectors and wherein the positioning strap is divided in multiple parts, which are mutually connected by the one or more elastic connectors.

15. Device according to claim 10, wherein at least one of the flexible surfaces is a rubber pad.

16. Device according to claim 15, wherein the rubber is electrically conductive.

17. Device according to claim 10, wherein the plurality of electrodes is divided in several arrays of electrodes.

18. Device according to claim 17, wherein the electrodes of at least one of the arrays are electrically connected to each other by means of metal foil.

* * * * *